United States Patent
Neelakantan

(10) Patent No.: US 7,391,847 B2
(45) Date of Patent: Jun. 24, 2008

(54) SYSTEM AND METHOD FOR DIVIDING IMAGES

(75) Inventor: Mahalingam Neelakantan, Karnataka (IN)

(73) Assignee: GE Medical Systems Information Technologies, Milwaukee, WI (US)

( * ) Notice: Subject to any disclaimer, the term of this patent is extended or adjusted under 35 U.S.C. 154(b) by 326 days.

(21) Appl. No.: 10/921,456

(22) Filed: Aug. 19, 2004

(65) Prior Publication Data

US 2006/0039531 A1 Feb. 23, 2006

(51) Int. Cl.
*G01N 23/04* (2006.01)
(52) U.S. Cl. ............... 378/62; 378/98.12; 378/901
(58) Field of Classification Search ............ 378/51–63, 378/210, 4, 901
See application file for complete search history.

(56) References Cited

U.S. PATENT DOCUMENTS

| | | | | |
|---|---|---|---|---|
| 5,334,851 A * | 8/1994 | Good et al. | ............ | 250/582 |
| 5,434,902 A * | 7/1995 | Bruijns | ............ | 378/98.7 |
| 5,818,064 A * | 10/1998 | Kohgami et al. | ............ | 250/580 |
| 6,256,372 B1 * | 7/2001 | Aufrichtig et al. | ............ | 378/41 |
| 6,359,961 B1 * | 3/2002 | Aufrichtig et al. | ............ | 378/41 |
| 6,424,692 B1 * | 7/2002 | Suzuki | ............ | 378/4 |
| 6,614,874 B2 * | 9/2003 | Avinash | ............ | 378/62 |
| 6,678,703 B2 * | 1/2004 | Rothschild et al. | ............ | 707/201 |
| 6,891,920 B1 * | 5/2005 | Minyard et al. | ............ | 378/37 |
| 7,116,807 B1 * | 10/2006 | Brackett | ............ | 382/128 |
| 7,152,785 B2 * | 12/2006 | Metz et al. | ............ | 235/380 |
| 7,209,578 B2 * | 4/2007 | Saito et al. | ............ | 382/128 |
| 2002/0087503 A1 * | 7/2002 | Judd et al. | ............ | 707/1 |
| 2003/0030004 A1 * | 2/2003 | Dixon et al. | ............ | 250/370.09 |
| 2003/0228041 A1 * | 12/2003 | Bae et al. | ............ | 382/131 |
| 2005/0063575 A1 * | 3/2005 | Ma et al. | ............ | 382/128 |
| 2005/0226375 A1 * | 10/2005 | Eberhard et al. | ............ | 378/62 |

\* cited by examiner

*Primary Examiner*—Edward J. Glick
*Assistant Examiner*—Alexander H Taningco
(74) *Attorney, Agent, or Firm*—Andrus, Sceales, Starke & Sawall, LLP

(57) ABSTRACT

System and method for dividing radiological images. The method can include sending a first request to an image acquisition system to perform a first examination, sending a second request to the image acquisition system to perform a second examination, and combining the first examination and the second examination into a single acquisition procedure. The method can also include acquiring images during the single acquisition procedure, tagging each one of the images with a protocol tag, and automatically dividing the images based on the protocol tag.

19 Claims, 1 Drawing Sheet

SYSTEM AND METHOD FOR DIVIDING IMAGES

BACKGROUND OF THE INVENTION

When more than one radiological examination must be performed on a patient, radiologists often perform a single acquisition procedure to acquire one set of images. The radiologist must then divide the images using a virtual examination split procedure. For example, a doctor may request a chest examination and an abdomen examination. The radiologist may acquire the images for both the chest and abdomen examinations during a single acquisition procedure. This has advantages for the patient, because the patient endures less waiting time and less radiation. The hospital's workflow is also improved because the imaging equipment and examination rooms are only set up and used once. However, the radiologist must manually divide the chest images from the abdomen images by performing the virtual examination split procedure. To manually divide the images, the radiologist must view each individual image and identify the portion of the patient's body shown in the image before determining with which examination the image is associated. The images from a single acquisition procedure must be manually divided into two or more individual examinations before the radiologist or the doctor can analyze and interpret the images.

With the number of images acquired for each examination rising dramatically (e.g., over 1000 images in one examination), it is becoming more difficult to manually divide the images. Also, with new technology, the images may not be in an order that corresponds easily to the individual examinations.

BRIEF DESCRIPTION OF THE INVENTION

One embodiment of the invention provides a method of automatically dividing radiological images acquired during a single acquisition procedure into sets of images for two or more radiological examinations. The method can include sending a first request to an image acquisition system to perform a first radiological examination, sending a second request to the image acquisition system to perform a second radiological examination, and combining the first radiological examination and the second radiological examination into a single acquisition procedure. The method can also include acquiring images during the single acquisition procedure and tagging each one of the images with a protocol tag. The method can further include automatically dividing the images based on the protocol tag.

DETAILED DESCRIPTION

Figure 1:
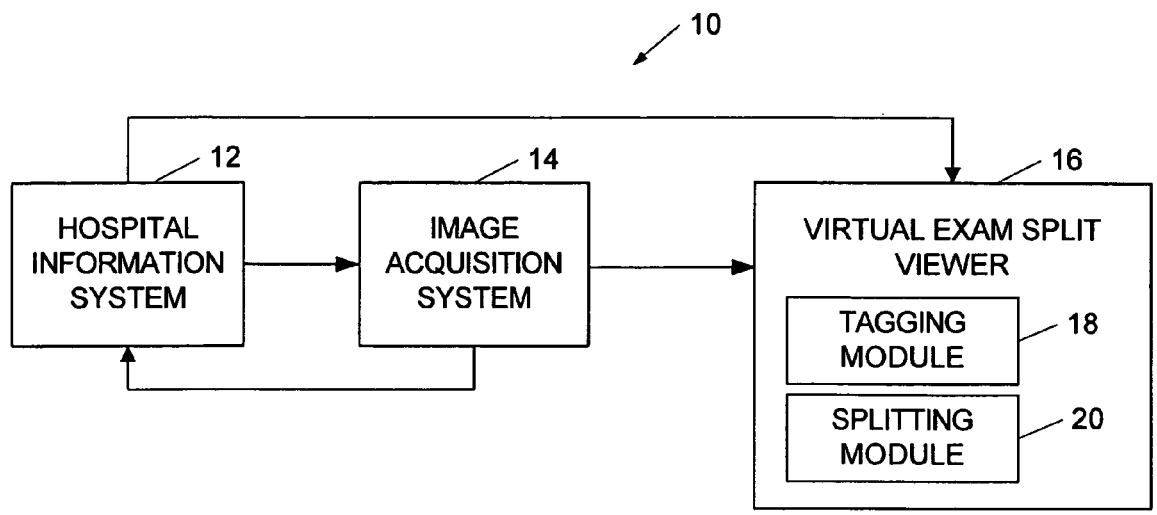
FIG. 1 is a schematic illustration of an imaging system according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates an imaging system 10 according to one embodiment of the invention. The imaging system 10 can include a hospital information system 12, an image acquisition system 14, and a virtual examination split viewer 16. The virtual examination split viewer 16 can include a tagging module 18 and a splitting module 20.

The hospital information system 12 can include a network of computers to collect, process, store, manage, and retrieve patient information, including radiological images. The hospital information system 12 can include a radiological information system (RIS) and/or a picture archiving and communication system (PACS).

The hospital information system 12 can be connected to the image acquisition system 14. The image acquisition system 14 can include any imaging device or modality that acquires a set of images of one or more portions of a patient's body. The image acquisition system 14 can include any one of a computed tomography system, a magnetic resonance imaging system, an X-ray system, an ultrasound system, any cardiac imaging systems, a nuclear medicine system, a positron emission tomography system, etc.

The image acquisition system 14 can be connected to the virtual examination split viewer 16. The virtual examination split viewer 16 can include an image browser that allows the radiologist to view the acquired images. The virtual examination split viewer 16 can automatically divide a set of images acquired during a single acquisition procedure into a set of images for each individual examination. The tagging module 18 of the virtual examination split viewer 16 can tag each one of the images with a protocol tag that is associated with a particular type of examination. The protocol tag can be embedded in the header of each one of the images. The protocol tag can include any suitable identification for a particular type of examination. For example, the protocol tag can be "tag r1" for a first type of examination and "tag r2" for a second type of examination. In another example, the protocol tag can be "<requestID>+<protocolID>." For this type of protocol tag, each request for a radiological examination is given a request identification and that request identification is associated with a protocol identification.

In one embodiment of the invention, the virtual examination split viewer 16 can embed the header of each image for one type of examination with the same protocol tag. For example, all of the images for a chest examination can include the protocol tag "tag r1" in their headers, while all the images for an abdomen examination can include the protocol tag "tag r2" in their headers. The splitting module 20 of the virtual examination split viewer 16 can automatically divide the images based on the protocol tag embedded in the header of each image. In other words, the splitting module 20 can automatically parse the image set according to the protocol tags.

Figure 2:
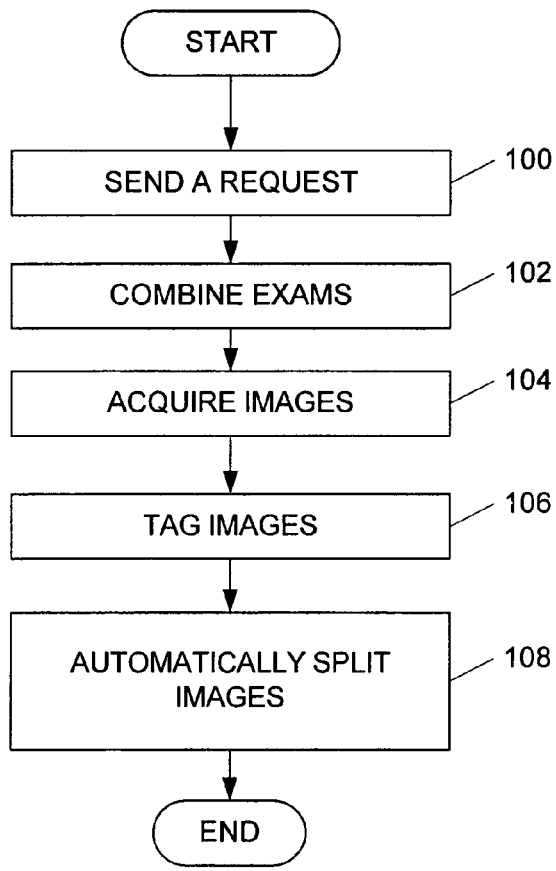
FIG. 2 is a flow-chart illustrating the operation of the imaging system of FIG. 1 according to one embodiment of the invention.

FIG. 2 is a flow-chart illustrating a method according to one embodiment of the invention. The hospital information system 12 can send (at 100) a first request to the image acquisition system 14 to perform a first radiological examination. The hospital information system 12 can send (at 100) a second request to the image acquisition system 14 to perform a second radiological examination. Alternatively, the hospital information system 12 can combine the first request and the second request into a single message that is sent (at 100) to the image acquisition system 14. The term "request" as used herein and in the appended claims can include one or more messages that indicate a doctor's desire to have a single or multiple radiological examinations performed on a patient.

The image acquisition system 14 can combine (at 102) the first radiological examination and the second radiological examination into a single acquisition procedure. The image acquisition system 14 can acquire (at 104) a single set of images from the patient.

The virtual examination split viewer 16 can tag (at 106) each one of the images with a protocol tag. The images can be tagged as the images are acquired or after all of the images have been acquired. In one embodiment, the tagging module 18 can embed a protocol tag into the header of each one of the images. The splitting module 20 can automatically divide (at 108) the images according to the protocol tags in the headers of the images. Once the images are divided, the radiologist (or any other clinicians) can view only those images that are associated with each particular examination. The radiologist can also view and interpret the images to ensure that the images have been divided correctly before committing the images to the picture archiving and communication system (PACS) of the hospital information system 12.

The following is an example of a method of the invention according to FIG. 2 with three examinations being requested. The hospital information system 12 can include three requests for examinations (Request 1, Request 2, and Request 3) in a single message to the image acquisition system 14. The image acquisition system 14 can interpret the message and assign an appropriate protocol to each request. The term "protocol" as used herein and in the appended claims refers to the positioning of the imaging device and the positioning of the patient in order for the imaging device to properly acquire the images for a particular examination. For example, a protocol for a computerized tomography cranial examination may include placing the patient supine with a towel or foam pad to separate the patient's head from the scanner cradle and preventing the patient's ears from touching the sides of the scanner cradle. The protocol for the computerized tomography cranial examination may also include positioning a computerized tomography machine to begin acquiring images at the patient's fillings and continue acquiring images superiorly completely through the frontal sinuses.

In computerized tomography systems, there is generally a one-to-one ratio between the request and the protocol. However, in other modalities, there may not be a one-to-one ratio between the request and the protocol. For example, in order to perform a complete cranial examination, the radiologist may need to follow a first protocol in which the patient is supine and a second protocol in which the patient is prone. To accommodate for those situations in which a one-to-one ratio between the request and the protocol does not exist, the image acquisition system 14 can assign tags to the images as follows:

Request 1-(Protocol 1, Protocol 2)-(image_1, image_2, . . . , image_k)-tag r1

Request 2-Protocol 3-(image_j, . . . , image_n)-tag r2

Request 3-Protocol 4-(image_x, . . . , image_z)-tag r3

In this example, the tagging module 18 embeds "tag r1" into the headers of the images (image_1, image_2, . . . , image_k) that are generated by Protocol 1 and Protocol 2. Similarly, the tagging module 18 embeds "tag r2" into the headers of the images (image_j, . . . , image_n) that are generated by Protocol 3. The splitting module 20 of the virtual examination split viewer 16 can scan the set of images and divide the images according to the protocol tags "tag r1," "tag r2," and "tag r3."

In some embodiments, the set of images including "tag r1" can be saved in the hospital information system 12 as being associated with Request 1 for the first type of examination. The sets of images including "tag r2" and "tag r3" can be saved in a similar manner as being associated with Request 2 for the second type of examination and Request 3 for the third type of examination.

Various features and advantages of the invention are set forth in the following claims.

The invention claimed is:

1. A method for dividing radiological images, the method comprising:

sending a first request to an image acquisition system to perform a first radiological examination of a first region of a patient;

sending a second request to an image acquisition system to perform a second radiological examination of a second region of the patient, wherein the first and second regions are two distinct regions of the patient;

combining the first radiological examination and the second radiological examination into a single acquisition procedure;

acquiring images during the single acquisition procedure;

tagging each one of the images with a protocol tag;

automatically dividing the images based on the protocol tag; and associating each of at least two protocols with either one of the first request and the second request and tagging each one of the images with a single protocol tag for the at least two protocols.

2. The method of claim 1 wherein the imaging acquisition system includes a computerized tomography system, and further comprising sending a first request having a one-to-one ratio with a first protocol and a second request having a one-to-one ratio with a first protocol.

3. The method of claim 1 and further comprising embedding the protocol tag in a header of each one of the images.

4. The method of claim 1 and further comprising automatically dividing images for the first radiological examination from images for the second radiological examination by parsing the images according to the protocol tag.

5. The method of claim 1 and further comprising sending the first request and the second request in a single message to the image acquisition system.

6. The method of claim 1 and further comprising acquiring images using at least one of a computed tomography, a magnetic resonance imaging system, an X-ray system, an ultrasound system, any cardiac imaging systems, a nuclear medicine system, and a positron emission tomography system.

7. The method of claim 1 and further comprising tagging each one of the images with a protocol tag including a request identification and a protocol identification.

8. A virtual examination split viewer for use with a hospital information system and an image acquisition system, the virtual examination split viewer comprising:
- a tagging module that tags acquired images with a protocol tag, wherein the acquired images are obtained by combining a first and a second exam request into a single examination request, and further wherein the first and second exam requests are for radiological images of two distinct regions of the patient; and
- a splitting module that automatically divides the acquired images by parsing the acquired images according to the protocol tag,
- wherein the tagging module associates each of at least two protocols with each of a first request and a second request, and tags each one of the acquired image with a single protocol tag for the at least two protocols.

9. The virtual examination split viewer of claim 8 wherein the imaging acquisition system includes a computerized tomography system, and wherein the hospital information system sends a request having a one-to-one ratio with a protocol to the tagging module.

10. The virtual examination split viewer of claim 8 wherein the tagging module embeds the protocol tag in a header of each one of the acquired images.

11. The virtual examination split viewer of claim 8 wherein the splitting module automatically divides images for a first radiological examination from images for a second radiological examination by parsing the acquired images according to the protocol tag.

12. The virtual examination split viewer of claim 8 wherein the image acquisition system includes at least one of a computed tomography system, a magnetic resonance imaging system, an X-ray system, an ultrasound system, any cardiac imaging systems, a nuclear medicine system, and a positron emission tomography system.

13. The virtual examination split viewer of claim 8 wherein the tagging module tags each one of the acquired images with a protocol tag including a request identification and a protocol identification.

14. A computer program embodied by a computer readable medium capable of being executed by a computer, the computer program for use in a system with a virtual examination split viewer and an image acquisition system, the computer program comprising:
- a tagging module that embeds headers of acquired images with protocol tags; and
- a splitting module that divides the acquired images by parsing the acquired images according to the protocol tags embedded in the headers, wherein the acquired images are obtained by combining a first and a second exam request into a single examination request, and further wherein the first and second exam requests are for radiological images of two distinct regions of the patient,
- wherein the tagging module associates each of at least two protocols with each one of a first request and tags each one of the acquired images with a single protocol tag for the at least two protocols.

15. The computer program of claim 14 wherein the imaging acquisition system includes a computerized tomography system, and wherein the hospital information system sends a request having a one-to-one ratio with a protocol to the tagging module.

16. The computer program of claim 14 wherein the tagging module embeds the protocol tag in a header of each one of the acquired images.

17. The computer program of claim 14 wherein the splitting module automatically divides images for a first radiological examination from images for a second radiological examination by parsing the acquired images according to the protocol tag.

18. The computer program of claim 14 where the image acquisition system includes at least one of a compound tomography system, a magnetic resonance imaging system, an X-ray system, an ultrasound system, any cardiac imaging systems, a nuclear medicine system, and a positron emission tomography system.

19. The computer program of claim 14 wherein the tagging module tags each one of the acquired images with a protocol tag including a request identification and a protocol identification.

* * * * *